United States Patent
Lim et al.

(10) Patent No.: US 8,339,449 B2
(45) Date of Patent: Dec. 25, 2012

(54) DEFECT MONITORING IN SEMICONDUCTOR DEVICE FABRICATION

(75) Inventors: Barbara Fong Chin Lim, Singapore (SG); Keng Heng Lai, Singapore (SG); Tanya Yang, Singapore (SG); Victor Seng Keong Lim, Singapore (SG); Fang Hong Gn, Singapore (SG); Liang Choo Hsia, Singapore (SG)

(73) Assignee: GLOBALFOUNDRIES Singapore Pte. Ltd., Singapore (SG)

( * ) Notice: Subject to any disclaimer, the term of this patent is extended or adjusted under 35 U.S.C. 154(b) by 669 days.

(21) Appl. No.: 12/537,269

(22) Filed: Aug. 7, 2009

(65) Prior Publication Data

US 2011/0032348 A1 Feb. 10, 2011

(51) Int. Cl.
*H04N 7/18* (2006.01)
(52) U.S. Cl. .................................. 348/126; 382/145
(58) Field of Classification Search .................. 348/125, 348/126; 382/145
See application file for complete search history.

(56) References Cited

U.S. PATENT DOCUMENTS

| 4,805,123 | A  | * | 2/1989 | Specht et al. ................. 382/144 |
| 5,608,453 | A  | * | 3/1997 | Gerber et al. .................... 348/87 |
| 6,169,282 | B1 | * | 1/2001 | Maeda et al. ................. 250/310 |
| 6,809,809 | B2 | * | 10/2004 | Kinney et al. .............. 356/237.5 |
| 7,831,083 | B1 | * | 11/2010 | Lauber .......................... 382/141 |
| 2001/0028732 | A1 | * | 10/2001 | Coulombe et al. ............ 382/149 |
| 2002/0088952 | A1 | * | 7/2002 | Rao et al. ................. 250/559.45 |
| 2004/0012775 | A1 | * | 1/2004 | Kinney et al. .............. 356/237.2 |
| 2008/0112608 | A1 | * | 5/2008 | Yang et al. .................... 382/149 |
| 2008/0226158 | A1 | * | 9/2008 | Abe et al. ..................... 382/149 |

* cited by examiner

*Primary Examiner* — Patrice Winder
(74) *Attorney, Agent, or Firm* — Horizon IP Pte Ltd (57) ABSTRACT

A method of forming a device is presented. The method includes providing a substrate containing at least a partially formed device thereon. The device comprises at least one defect site. A pixilated image of the defect site is acquired, and each pixel comprises a grey level value (GLV). Surrounding noises of the defect site is eliminated. A point of the image is identified as the center of the defect. A plurality of iterations to exclude outer edge pixels surrounding the center of the defect image is performed. The defect is categorized as a killer or non-killer defect.

20 Claims, 12 Drawing Sheets

DEFECT MONITORING IN SEMICONDUCTOR DEVICE FABRICATION

BACKGROUND

In the fabrication process of electronic devices, for instance, integrated circuits (ICs), it is essential to detect defects effectively at an early stage in order to maintain and improve yield rates. Charge particle beam systems such as electron beam inspection (EBI) systems, are being widely implemented in in-line defect monitoring. EBI systems are able to detect electrical failures such as open and leakage defects through the use of voltage contrast (VC).

Image comparison techniques are commonly used for defect detection in IC manufacturing processes. Typically, charged particle microscope images for a "defect site" and a "reference site" are acquired. Every image comprises a plurality of pixels, with each pixel being defined by its location within the image. The two images are aligned pixel-by-pixel. Pixel grey level variations are then obtained by comparing or subtracting their surface charge induced grey levels or intensities. Grey level value (GLV) is determined by taking the maximum GLV from the "defective site" pixels. For some defects, for example, leakage defects which cause bright voltage contrast (BVC), the real GLV can be distorted by surrounding charging effects or noises, resulting in inaccurate and inconsistent GLV based on one pixel. Therefore, challenges for charge particle beam inspectors to distinguish killer and non-killer defects exist.

SUMMARY

A method of forming a device is presented. The method includes providing a substrate containing at least a partially formed device thereon. The device comprises at least one defect site. A pixilated image of the defect site is acquired, and each pixel comprises a grey level value (GLV). Surrounding noises of the defect site is eliminated. A point of the image is identified as the center of the defect. A plurality of iterations to exclude outer edge pixels surrounding the center of the defect image is performed. The defect is categorized as a killer or non-killer defect.

In another embodiment, a method of forming a device is presented. The method includes providing a substrate containing at least a partially formed device thereon. The device comprises at least one defect site. A pixilated image of the defect site is acquired, and each pixel comprises a grey level value (GLV). Surrounding noises of the defect site is eliminated. A point of the image is identified as the center of the defect. The center of the defect includes one pixel or adjacent pixels having the highest GLV in a BVC defect site, or one pixel or adjacent pixels having the lowest GLV in a DVC defect site. A plurality of iterations to exclude outer edge pixels surrounding the center of the defect image is performed. The defect is categorized as a killer or non-killer defect.

In yet another embodiment, a system for monitoring defects is disclosed. The system includes means for providing a substrate containing at least a partially formed device thereon. The device comprises at least one defect site. The system also includes means for acquiring a pixilated image of the defect site selected. Each pixel comprises a grey level value (GLV). Means for eliminating surrounding noises of the defect site and means for identifying a point of the image as the center of the defect are also included. In addition, means for performing a plurality of iterations to exclude outer edge pixels surrounding the center of the defect image, as well as means for categorizing the defect as a killer defect or a non-killer defect are also included.

These and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Embodiments generally relate to semiconductor devices, for example, integrated circuits (ICs). The ICs can be any type of IC, such as dynamic or static random access memories, signal processors, or system-on-chip devices. In order to achieve high yield in the semiconductor devices manufacturing, it is essential for in-line electrical defect monitoring systems to provide timely and accurate feedbacks on the defects and yield detractors for corrective actions to be taken.

Figure 1:
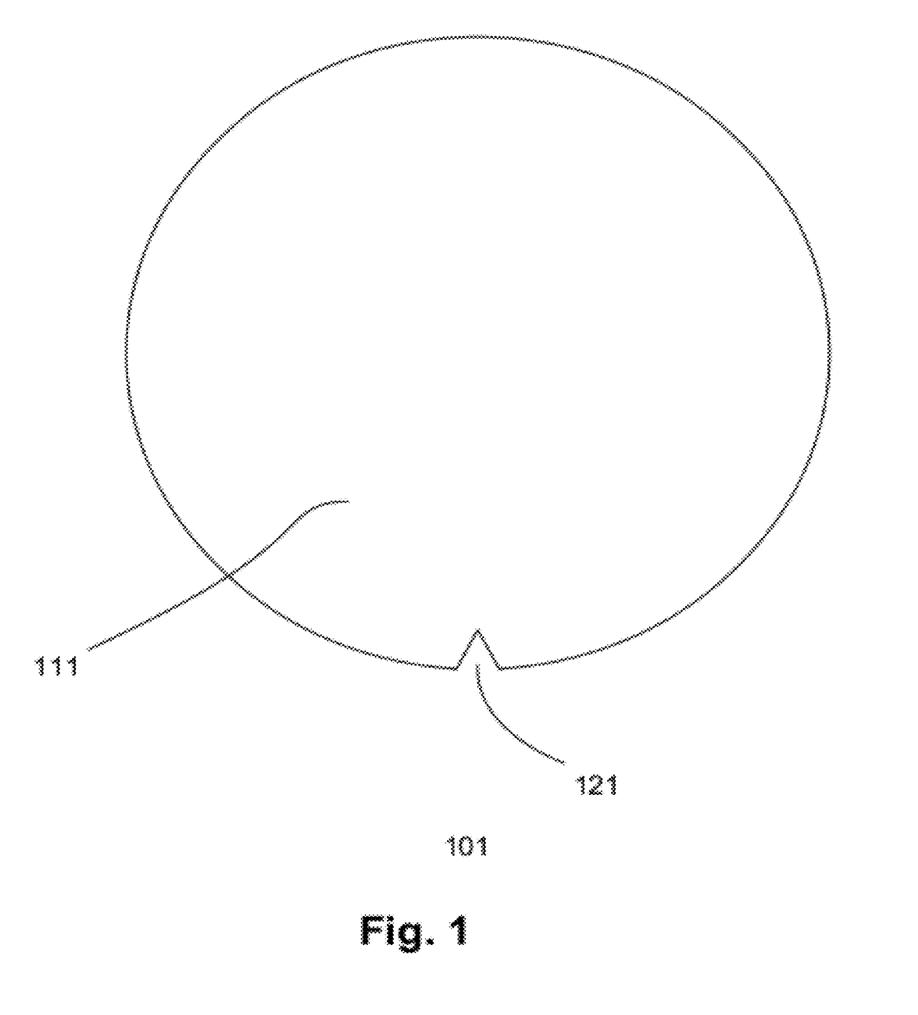
FIG. 1 shows a semiconductor wafer.

FIG. 1 shows a semiconductor wafer 101. The semiconductor wafer, for example, comprises silicon. Other types of semiconductor wafers are also useful. For example, the semiconductor wafer may be a p-type, n-type, silicon-on-insulator or silicon germanium wafer. The semiconductor wafer may include a notch 121 to indicate the crystal orientation of the wafer. Other techniques for indicating the crystal orientation may also be useful. Additional indicators may also be included to indicate the dopant type of the wafer.

The wafer includes an active surface 111 on which devices are formed. The fabrication of devices or integrated circuits (ICs) involves the formation of features on a substrate that make up circuit components, such as transistors, resistors and capacitors. The devices are interconnected, enabling the device to perform the desired functions. Interconnections are formed by forming contacts and conductive lines in a dielectric layer using, for example, damascene techniques. A plurality of devices are formed on the wafer in parallel. The devices are subsequently singulated, assembled and tested.

During the development or fabrication phase, defects may occur. Defects, for example, may include electrical defects, such as short or open connections, which result in current leakage or high resistance.

Figure 2:
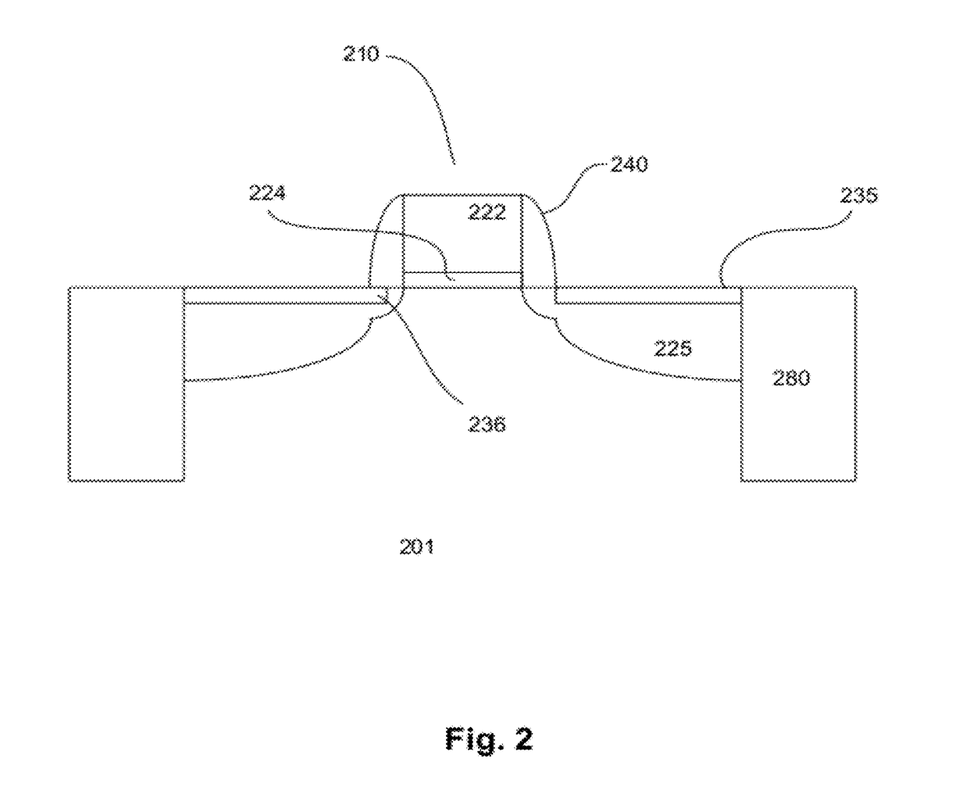
FIGS. 2-3 show different types of defects for analysis.

FIG. 2 shows a type of defect which may occur during fabrication. A portion 201 of a wafer is shown. The wafer includes an active region in which a transistor 210 is formed. Isolating the active region from other regions are isolation regions 280, for example, shallow trench isolation (STI) regions. The transistor includes a gate. The gate, for example, includes a gate electrode 222 over a gate dielectric layer 224. Sidewall spacers 240 are provided on sidewalls of the gate. Source/drain diffusion regions 225 are disposed in the active region adjacent to the gate. Silicide contacts 235 are provided on the source/drain diffusion regions. The silicide contacts, for example, may be nickel silicide. However, in the formation of the silicide contacts, piping 236 may occur. Piping refers to the extension of the silicide beneath the spacer, which can cause current leakage.

Figure 3:
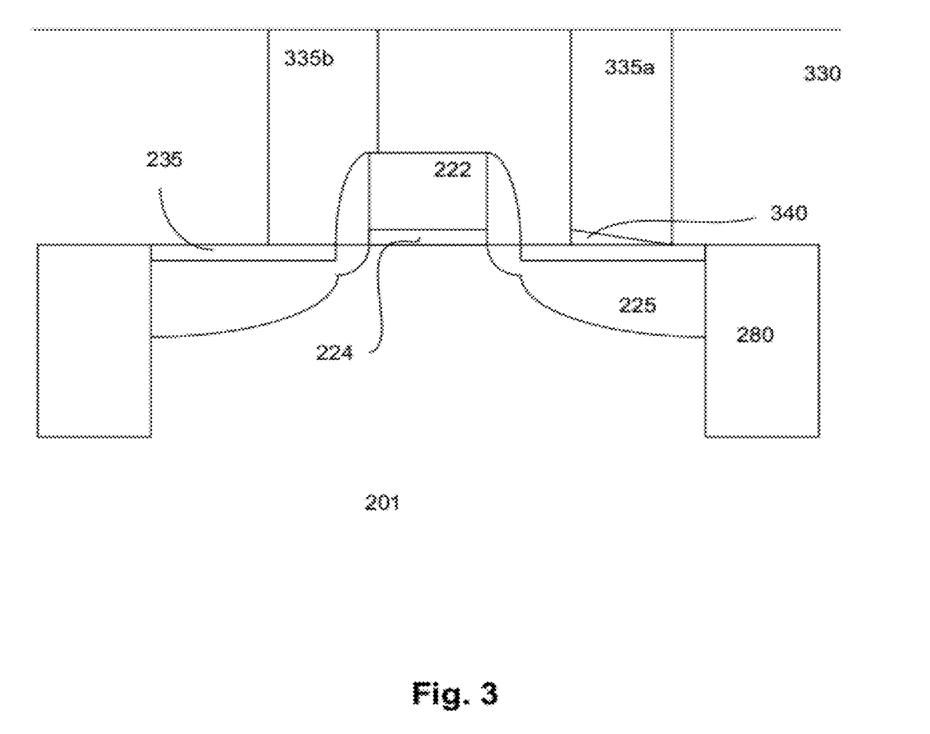

FIG. 3 shows another type of defect which may occur during fabrication. As shown, a transistor is provided in an active region, like in FIG. 2. A dielectric layer 330 is formed over the transistor. First and second contact plugs 335a-b are formed in the dielectric layer to provide electrical contact to the source/drain regions. The contact plugs, for example, comprise tungsten. Other types of conductive material may also be useful.

To form the contact plugs, vias are etched into the dielectric layer and subsequently filled with a conductive material. A liner or liners may be provided in the contact vias. The conductive material is then polished by, for example, chemical mechanical polishing (CMP) to form a planar top surface.

As shown, the first contact plug 335a has a void 340 between the conductive material and silicide contact. The void creates a weak connection, which results in a high resistance defect. The second contact plug 335b is misaligned to the source/drain diffusion region. This may result in a short between the gate electrode and source/drain diffusion region, causing current leakage. It is further understood that other types of leakage mechanism can also be detected. For example, fault induced leakage, implant damage induced leakage or other types of leakage can be detected.

Figure 4:
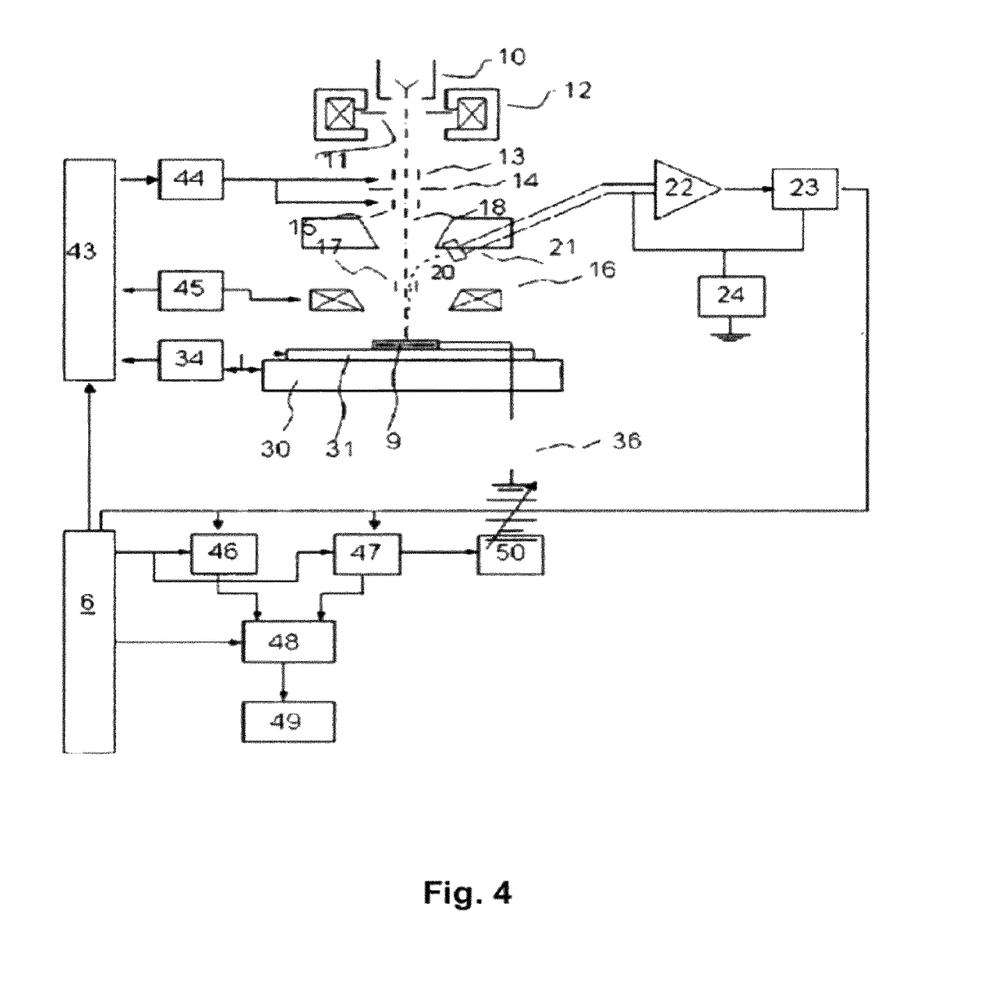
FIG. 4 shows an inspection system.

FIG. 4 shows a charge particle beam system. In one embodiment, the charge particle beam system comprises an electron beam inspection (EBI) system. The EBI system, for example, can be an HMI eScan3xx EBI system. Other types of EBI systems may also be useful.

The system, in one embodiment, comprises a primary electron beam source, a secondary electron detection portion, an image processing portion, and a system control portion. The primary electron beam source portion, for example, includes an electron gun 10, a beam extraction electrode 11, a condenser lens 12, a beam blanking deflector 13, an aperture 14, a scanning deflector 15, and an objective lens 16. The secondary electron detection portion can include an E×B electron detour device 17, a secondary electron detector 21, a preamplifier 22, an A/D converter 23, and a high voltage electric source 24. The image processing portion, for example, includes a first image storage 46, a second image storage 47, an arithmetic operation device 48, a defect judgment device 49, and a monitor 50. The system control portion may include a microprocessor computer 6, a position correction and control circuit 43, a stage driver 34, an objective lens source 45, a scan deflector signal generator 44, a sample stage 30, a X-Y direction stage 31, and a high voltage electric source 36.

An article, such as a wafer, which is to be inspected is placed on the sample stage. The wafer is irradiated by the primary electron beam. The secondary electron 20 emanating from the substrate surface 9 is detoured by the E×B electron detour device 17 to the detector 21, the electron signal is then being amplified and converted to digital signal for further image processing and defect judgment. The wafer is translated in the x-y direction to inspect the complete wafer.

Figure 5A:
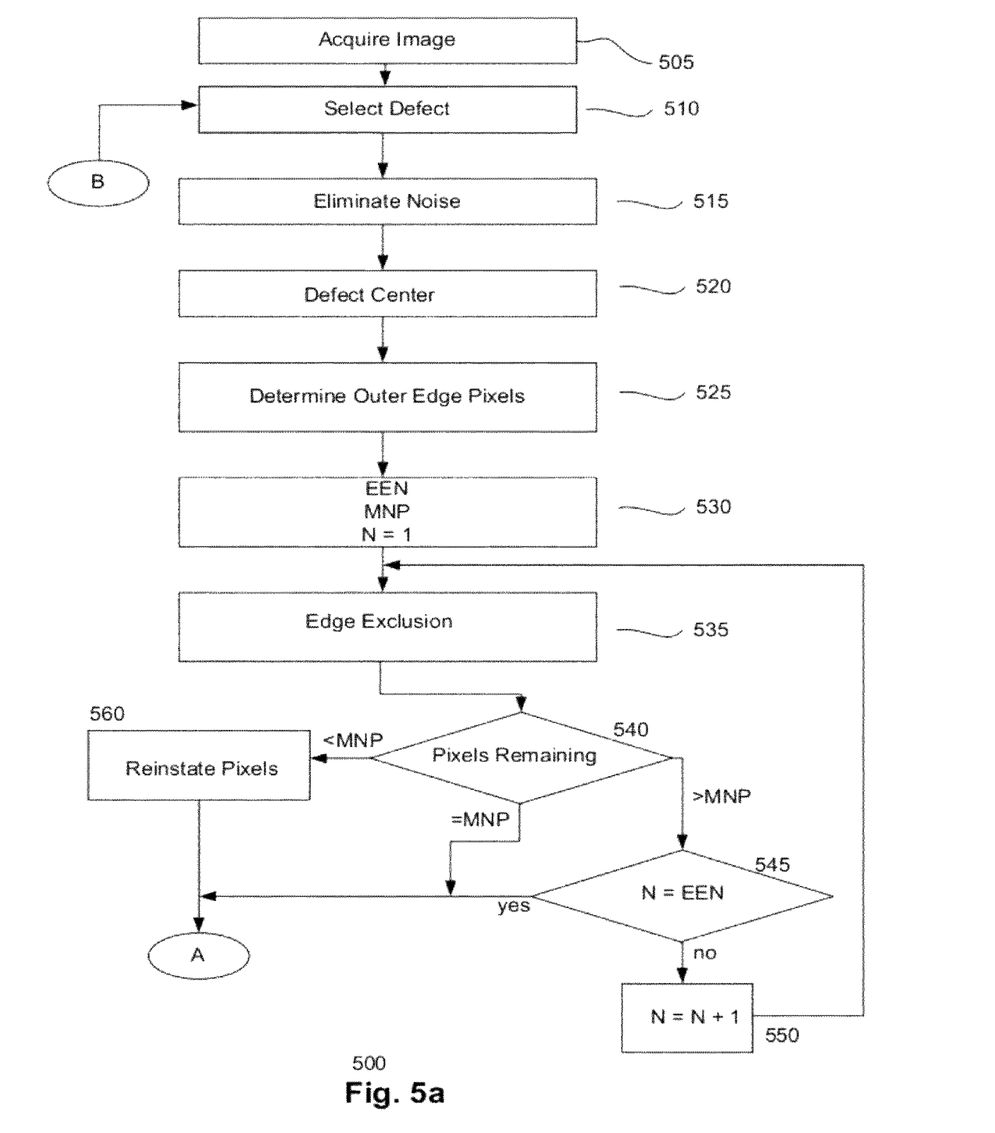
FIGS. 5a-b show an embodiment of a process for defect detection.
Figure 5B:
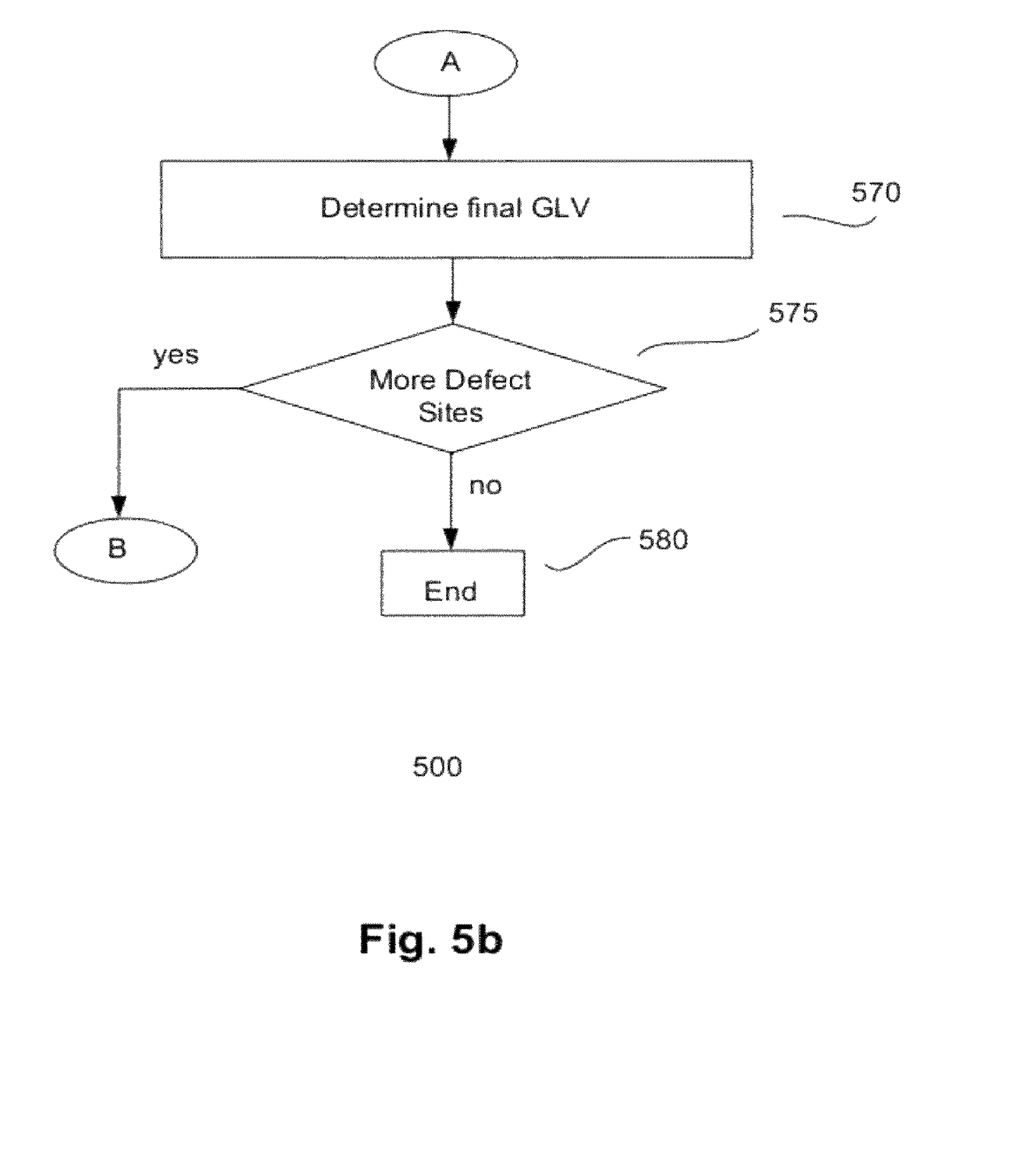

FIGS. 5a-b show an embodiment of a process 500 for detecting defects in an article. The article, for example, is a semiconductor wafer, such as that described in FIG. 1. Detecting defects in other types of articles is also useful. The semiconductor wafer can be at various stages of processing. For example, the semiconductor wafer can be at processing to form interconnects. For example, the semiconductor wafer can be at a stage subsequent to chemical mechanical polishing of conductive material, such as tungsten, to form tungsten plugs. Alternatively, the conductive material may be copper for forming, for example, interconnects. Detecting defects in a wafer at other stages of processing is also useful. For example, the defects may be shorted or open connections.

An image of the article is obtained at step 505. The image, for example, comprises an image of the active surface of the wafer on which devices are formed. In an alternative embodiment, the image can be an image of a portion of the wafer. For example, the image can be of a specific die or specific dies on the wafer or even a specific portion of a die or some dies. Other configurations of the image may also be useful. In one embodiment, defects are detected by an EBI system, such as one described in FIG. 4. Other types of inspection systems can also be useful.

The acquired image, in one embodiment, comprises a plurality of pixels. The pixel size of the image acquisition can be selected to produce a defect site which comprises a plurality of pixels. For example, the pixel size is selected to produce a defect site with an average of at least 5 pixels in the x and y directions. The pixel size can be selected by setting the inspector tool appropriately. Preferably, the defect site produces an average of at least 9 pixels in the x and y directions. Selecting a pixel size which produces other number of pixels in the x and y directions may also be useful. It is understood that the number of pixels in the x and y directions do not have to be equal. The number of pixels in a defect site is inversely related to the pixel size. For example, smaller pixel size produces higher number of pixels per image, which increases image resolution. Conversely, larger pixel size produces lower number of pixels per image, which decreases image resolution.

The pixels correspond to the spatial locations within the image. Each pixel will be associated with a grey level (GL). In one embodiment, the pixels can have a GL value (GLV) between 0-255. Providing other number of GLVs is also useful. For example, the GLV can be $2^n$, wherein n is a whole number corresponding to the number of bits allocated.

The range of GLVs can be divided into first and second portions. For example, the first portion can be associated with bright voltage contrast (BVC) levels and the second portion can be associated with dark voltage contrast (DVC) levels. In one embodiment, the lowest value may correspond to completely dark level (e.g., 0) while the highest value may correspond to completely bright level (e.g., 255). One of the GLVs can be designated as the transition level between BVC and DVC.

In one embodiment, BVC levels may correspond to leakage current magnitudes while DVC levels correspond to resistance magnitudes. For example, the greater the GLV from the transition level, the higher the magnitude of leakage current; the lesser the GLV from the transition level, the higher the magnitude of resistance.

Figure 11:
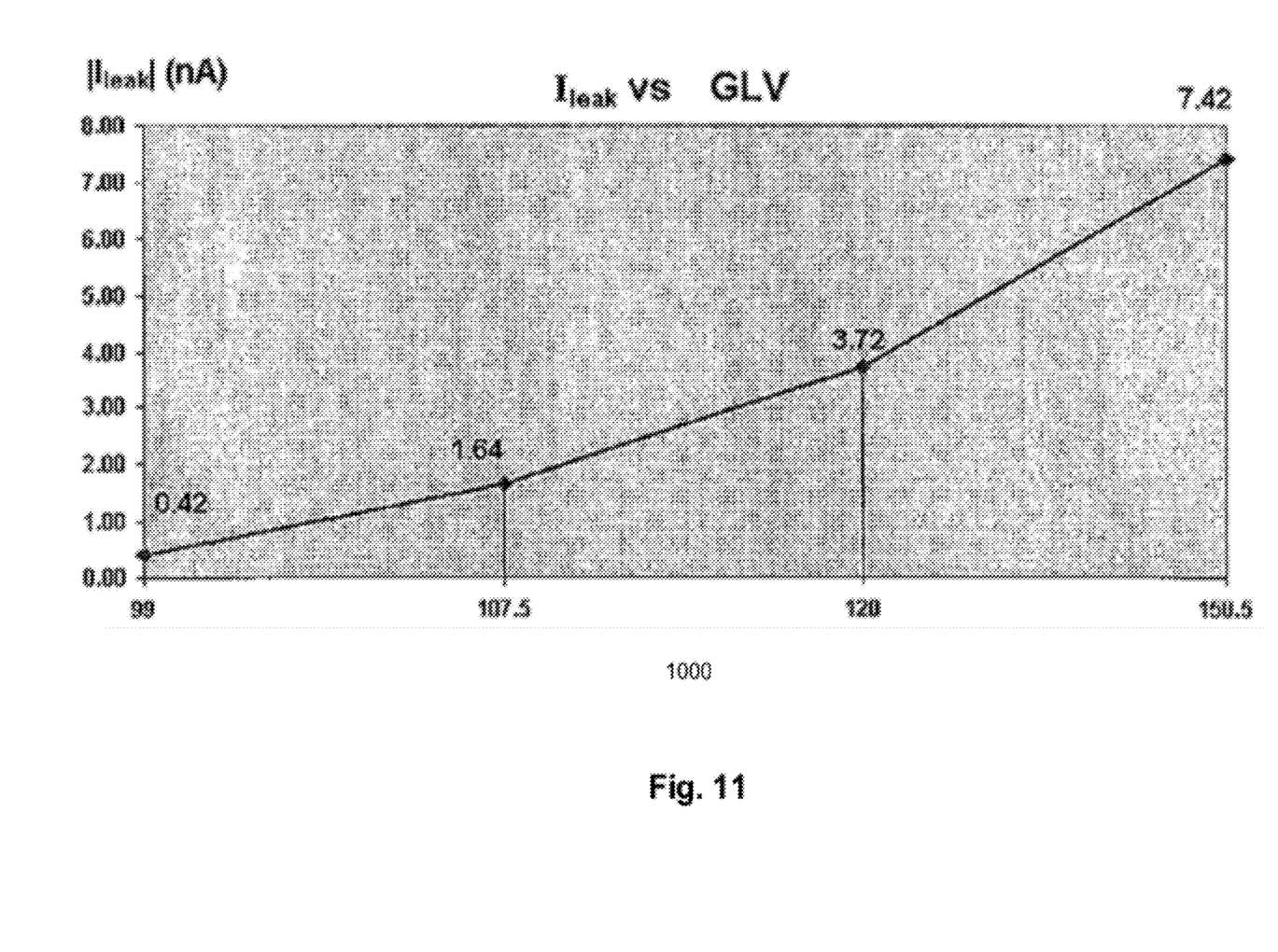
FIG. 11 shows a graph correlating GLV with leakage current.

FIG. 11 shows a graph 1000 correlating leakage current to GLV. As shown, a GLV of 99 correlates to a leakage current of 0.42 nA, a GLV of 107.5 correlates to a leakage current of 1.64 nA, a GLV of 120 correlates to a leakage current of 3.72 nA and a GLV of 150.5 correlates to a leakage current of 7.42. Clearly, the magnitude of the leakage current is directly related to the brightness of the pixel or magnitude of the GLV.

Figure 6:
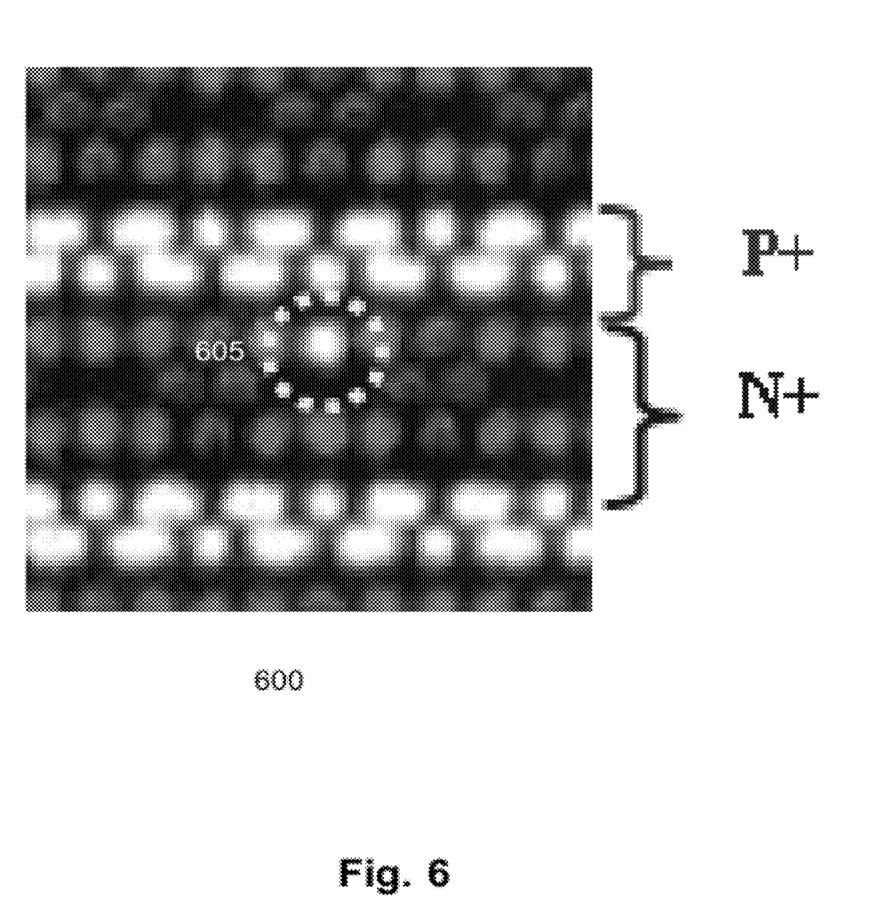
FIG. 6 shows a defect on a wafer.

Once the image of the wafer is acquired, it is examined to determine if there are defects. For example, the image may have numerous BVC and DVC defects. FIG. 6 shows a SEM of a portion of semiconductor wafer 600 with a BVC defect. The wafer comprises P+ regions which are bright and N+ regions which are dark. Providing P+ regions which are dark and N+ regions which are bright is also useful. This can be achieved by reversing the surface bias or landing energy. As shown, the N+ region includes a bright spot 605, indicating a defect. The defect, in one embodiment, represents a short or leakage at the contact plug. Other types of defects are also useful.

Figure 7A:
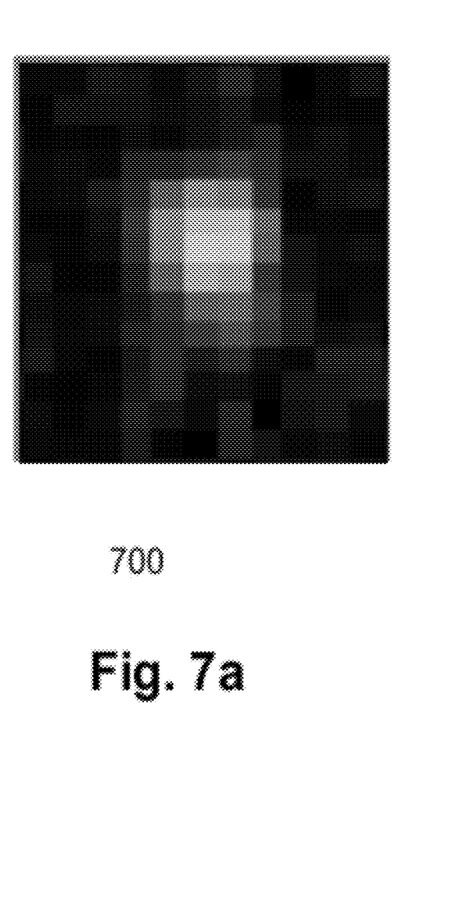
FIGS. 7a-b show an image of a defect site and corresponding schematic image.
Figure 7B:
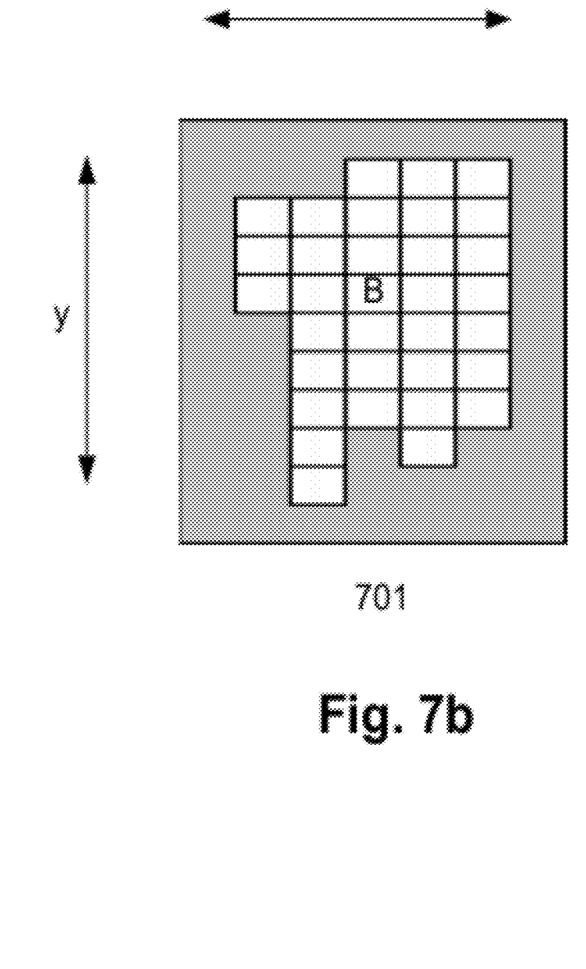

FIG. 7*a* shows an image 700 of a defect site and FIG. 7*b* shows its corresponding schematic image 701. The defect site is the defect site as shown in FIG. 6. The image comprises a plurality of pixels in the x and y directions. The maximum number of pixels in the x direction is 5 while the maximum number of pixels in the y direction is 8. The pixels vary in different GLV levels above the threshold value.

Going back to FIGS. 5*a-b*, a defect site is selected for analysis at step 510. In one embodiment, the defect site comprises a BVC defect site. Selecting a DVC defect site may also be useful. Analysis can be performed inline by the inspector tool. For example, the software in the inspector tool can be tailored to perform the analysis inline. Alternatively, the analysis can be performed offline.

At step 515, the selected site is processed to eliminate surrounding noises. In one embodiment, a noise threshold value (NTV) is defined. The NTV determines the pixels to be eliminated from the defect site. For example, in a BVC defect site, pixels having GLV less than the NTV are eliminated. Conversely, pixels having GLV greater than the NTV are eliminated in a DVC defect site. In the event that all pixels in the defect site are eliminated as a result of the NTV, the defect site is re-categorized as a non-defect site. The NTV can be determined or derived from historical data, test wafers or characterization of wafers having intentional defects and known good sites.

In one embodiment, a bright NTV (BNTV) is defined for BVC defect sites and a dark NTV (DNTV) is defined for DVC defect sites. The BNTV can be, for example, about 20-60 while the DNTV can be about 150-180. Other BNTVs and DNTVs are also useful. In other embodiments, the BNTV and DNTV may be the same. For example, the NTV for both BVC and DVC can be about 20 to 100. Other NTV values such as 80-120 can also be used for both BVC and DVC defect sites.

Figure 8A:
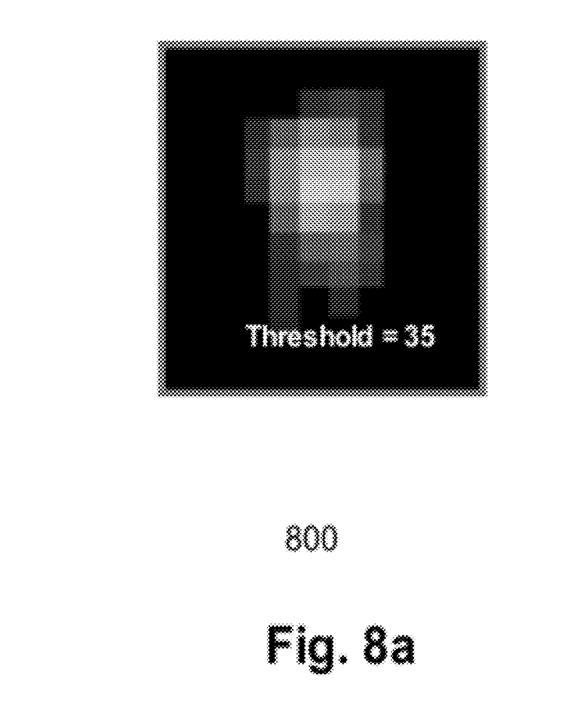
FIGS. 8a-b show an image of a defect site and corresponding schematic image after processing with a threshold value.
Figure 8B:
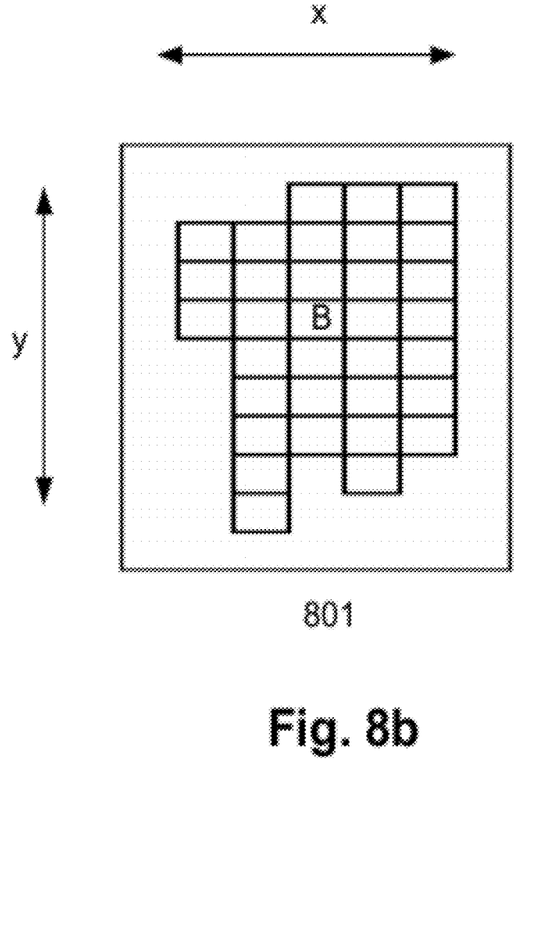
Figure 9A:
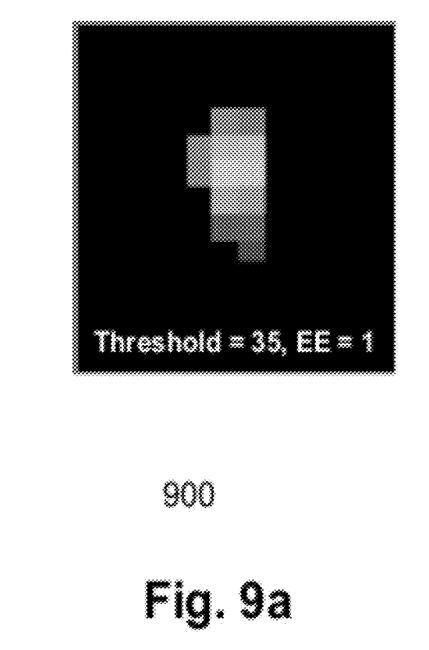
FIGS. 9a-b and 10a-b show images of a defect site and corresponding schematic images with edge exclusion of 1 and 2, respectively.
Figure 9B:
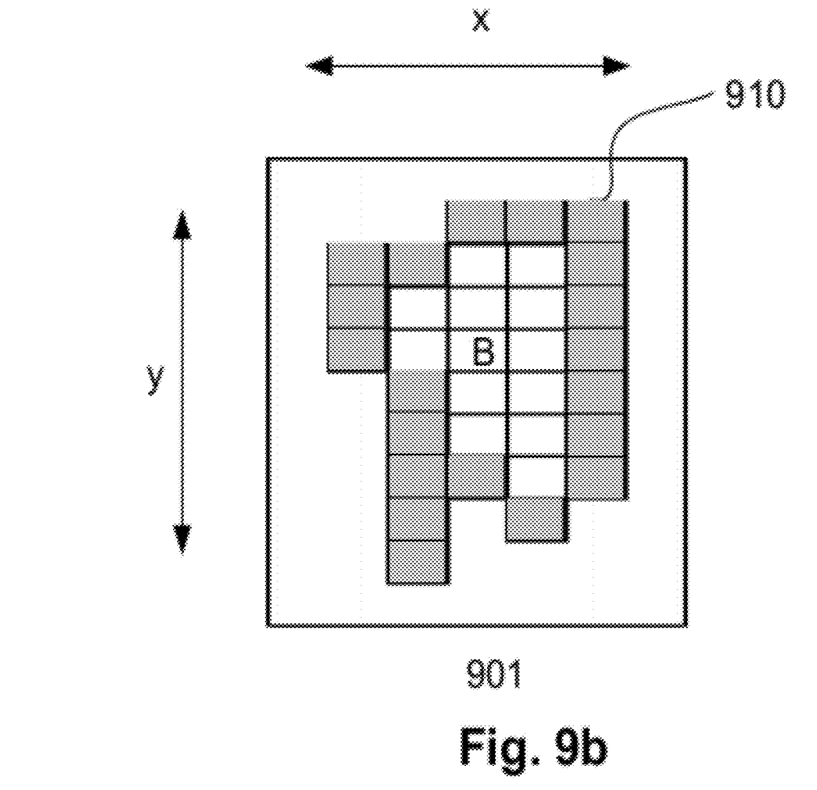
Figure 10A:
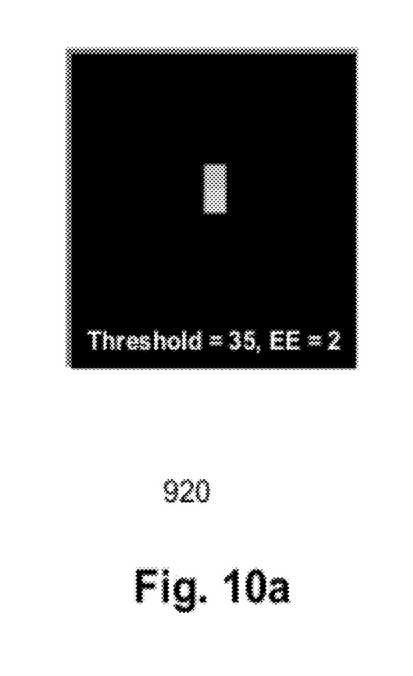
Figure 10B:
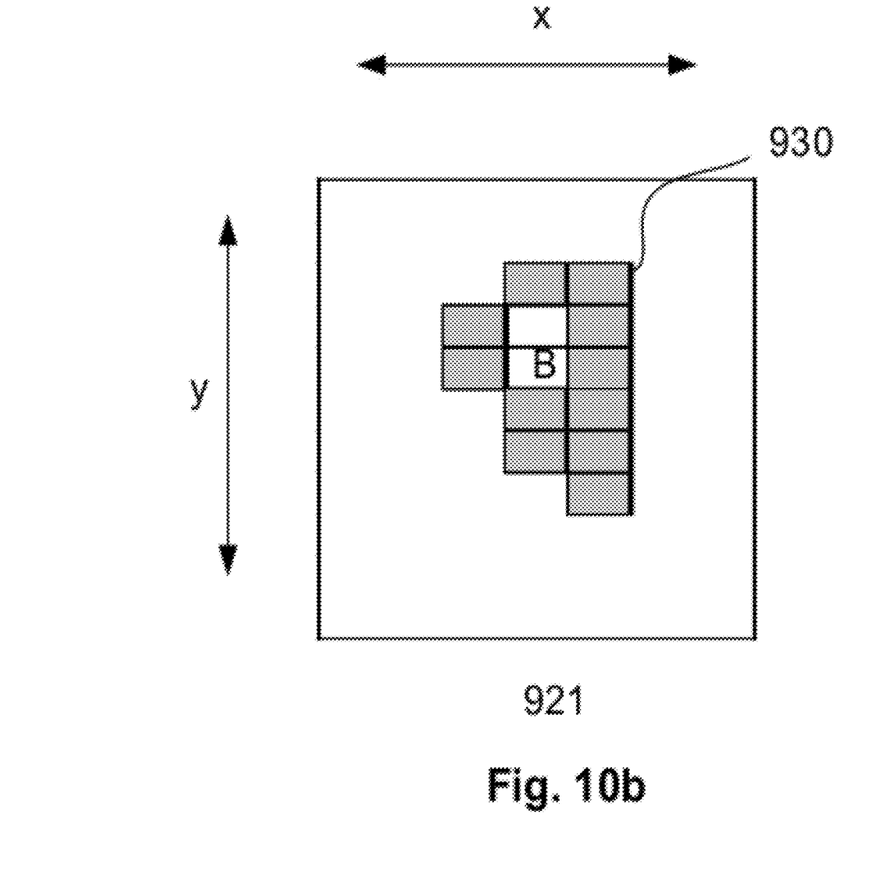

FIG. 8*a* shows an image 800 of a BVC defect site and FIG. 8*b* shows its corresponding schematic image 801. The defect site is the defect site as shown in FIG. 6. The image comprises a plurality of pixels in the x and y directions. The image is processed with a BNTV value of 35. For example, pixels having a GLV of 35 or less are removed from the image.

Referring back to FIGS. 5*a-b*, the pixel or pixels with the highest GLV are identified at step 520. The defect site in FIG. 7*b* or FIG. 8*b* shows only one pixel (B) with highest GLV. However, it is understood that a defect site may contain more than one pixel with the highest GLV. For example, adjacent pixels may have the same GLV. In one embodiment, the point of the image with pixels having the highest GLV corresponds to the center of the defect.

In one embodiment, at step 525, the image is processed to determine outer edge pixels of the defect site. The outer edge pixels can be those pixels which have a precipitous decrease in GLV with respect to the center of the defect (e.g., brightest pixel or pixels). For example, the outer edge pixels may be those pixels which have a greater than 30% change in GLV with respect to the brightest pixel. The resulting image after the edge pixels are determined may include rows and columns with different numbers of pixels.

An edge exclusion number (EEN), in one embodiment, is defined at step 530. The EEN indicates the number or iterations of edge exclusion processes to be performed. For example, if EEN is equal to 3, three edge exclusion processes are performed. An edge exclusion process comprises removing end pixels of each column and each row of the image.

In one embodiment, the EEN can be any whole number greater than or equal to 1. The EEN should be any whole number for which at least one or some pixels remain in the processed image. For example, the EEN can be any whole number less than or equal to the radius from the center of the defect image. The radius, for example, can be taken as the shortest radius from the center. In one embodiment, the EEN can be any whole number except zero which is less than the radius from the center of the defect image. Preferably, the image allows for an EEN of at least about 3-4. Other EEN values are also useful. In one embodiment, prior to the commencement of any edge exclusion processing, N is set to 1, where N is equal to the iteration to be performed.

At step 535, edge exclusion processing is performed. Edge exclusion processing is repeated until N=EEN. Depending on the value of EEN, one or more rows and/or columns may be eliminated, leaving at least the pixel or pixels at or near the center of the image remaining.

In one embodiment, a safeguard can be incorporated such that a minimum number of pixels (MNP) remain after edge exclusion processing, regardless of the value of the EEN defined. For example, the MNP can be defined at step 530. The MNP, in one embodiment, is equal to at least 1. In other embodiments, the MNP can be at least about 4 or about 4-8. Providing other MNP values is also useful.

For example, after an iteration of edge exclusion at step 535, the image is analyzed to determine the number of pixels remaining at step 540. In one embodiment, if the number of pixels remaining in the image is equal to MNP, the edge exclusion processing terminates regardless of the value of N. In another embodiment, if the number of pixels remaining is less than MNP, the edge exclusion processing terminates regardless of the value of N. Additionally, the pixels removed in the current iteration of edge exclusion processing which resulted in the number of pixels in the image to be less than MNP are reinstated into the image. In other embodiments, the number of pixels reinstated results in the image having the number of pixels equal to MNP. For such embodiments, the pixels with the highest or higher GLVs are reinstated before the lower ones. After reinstating the removed pixels or one or some of the removed pixels, the edge exclusion processing terminates. In yet other embodiments, the edge exclusion process can be terminated if there is at least one pixel remaining, regardless of MNP. Other configurations of safeguards can also be implemented. After terminating the edge exclusion processing, the process proceeds to step 570.

If the number of pixels remaining in the processed image is greater than MNP, the value of N is compared with EEN at step 545. If N is not equal to EEN, for example, N is less than EEN, the value of N is incremented at step 550 and repeats edge exclusion processing at step 535. On the other hand, if the value of N is equal to EEN, edge exclusion processing of the image is completed and proceeds to step 570.

At step 570, the GLVs of the remaining pixels in the defect image are averaged to define the final GLV (FGLV) or defect GLV (DGLV) for the defect site. The FGLV is used to categorize the defect at step 575. In one embodiment, based on the FGLV, the defect can be determined as a killer defect or non-killer defect. In one embodiment, if the FGLV is outside of the acceptable range defined by a threshold DGLV, the defect site is categorized as a killer defect. On the other hand, if the FGLV is within the acceptable range defined by the threshold DGLV, the defect is categorized as a non-killer or marginal defect.

In one embodiment, for BVC sites, a FGLV which is greater than the threshold DGLV is categorized as a killer defect while below or equal to the threshold DGLV is categorized as a non-killer defect. For DVC sites, a FGLV which is less than the threshold DGLV is categorized as a killer defect while above or equal to the threshold DGLV is categorized as a non-killer defect. The threshold DGLV can be determined from historical test data measured from test wafers, for example, having intentional defects and known good sites.

Furthermore, the type of defects can be ascertained based on the FGLV. To determine or correlate a FGLV to a type of defect, metrological techniques can be employed. For example, correlation and calibration can be performed based on C-AFM or nano-probing with respect to GLV. Other techniques for correlating and/or calibrating GLV can also be used.

The process, at step 575 determines if there are other defect sites to be analyzed. If there are, the process returns to step 510. If there are no other defect sites to be processed, the process terminates at step 580. It is understood that at least some of the sequence of process steps can be altered according to the user's preference.

In an alternative embodiment, the measured GLV or DGLV of a pixel in the image is subtracted by a reference GLV (RGLV) to arrive at the GLV. That is, GLV=DGLV−RGLV. The RGLV can be obtained, for example, from a reference die. By subtracting the DGLV from RGLV, negative and positive GLVs can be obtained for a pixel. For example, a negative GLV may relate to a DVC, a positive GLV may relate to a BVC and 0 is the transition between DVC and BVC. In such case, the greater the GLV, the higher the magnitude of leakage current. On the other hand, the more negative the GLV, the higher the magnitude of resistance.

For such applications where there can be positive or negative GLV, the outer edge cells of the image in step 525 can be determined when there is a change in polarity. Other process steps for such applications remain similar, taking into account of the polarity differences.

We have found that the edge cells are most susceptible to surface charging or noise which renders the measured values unstable. That is, the measured values may not be repeatable or consistent. By eliminating these unstable pixels, more stable and repeatable DGLV distribution can be obtained.

FIGS. 9a-b and 10a-b show images and corresponding schematic images of a defect site after edge exclusion of 1 and 2, respectively. As shown, after edge exclusion, the number of pixels in the image is reduced. For example, after one edge pixel 910 is removed from each end of each row and column of pixels, 13 pixels remain in the image. After two edge pixels 930 are removed from each end of each row and column of pixels, 2 pixels remain. In either case, the center pixel remains.

Additionally, as described, the final GLV from the site of interest is determined by the average GLVs of the remaining pixels of the site after processing. This has been found to further enhance stability and repeatability of GLV distribution.

Identification of the defects can be on production wafers during the fabrication process of devices to determine defective dies from good dies. The good dies will be processed to completion to form devices. Also, dies with non-killer defects can be completed to form sub-standard devices.

In other embodiments, the identification of defects can also be used to determine root causes of defects in the manufacturing process. Once the root causes are determined, the manufacturing process may be modified to correct for the defects.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A method of forming a device comprising:
providing a substrate containing at least a partially formed device thereon, wherein the device comprises at least one defect site;
acquiring a pixilated image of the defect site selected, wherein each pixel comprises a grey level value (GLV);
eliminating surrounding noises of the defect site;
identifying a point of the image as the center of the defect;
performing a plurality of iterations to exclude outer edge pixels surrounding the center of the defect image; and
categorizing the defect as a killer defect or a non-killer defect.

2. The method of claim 1 wherein eliminating surrounding noises comprises:
defining a bright noise threshold value (BNTV) in a bright voltage contrast (BVC) defect site, eliminating pixels having GLV less than the BNTV; or
defining a dark noise threshold value (DNTV) in a dark voltage contrast (DVC) defect site, eliminating pixels having GLV greater than the DNTV.

3. The method of claim 2 wherein the center of the defect comprises:
one pixel or adjacent pixels having the highest GLV in a BVC defect site; or
one pixel or adjacent pixels having the lowest GLV in a DVC defect site.

4. The method of claim 3 wherein the outer edge pixels comprises pixels with a drastic change in GLV with respect to the center of the defect.

5. The method of claim 4 wherein excluding outer edge pixels comprises:
defining an edge exclusion number (EEN) to indicate the number of iterations of edge exclusion processes to be performed,
wherein the EEN comprises a whole number except zero which is less than the radius from the center of the defect image.

6. The method of claim 4 further comprises:
defining a minimum number of pixels (MNP) remain after edge exclusion processing;
comparing the number of pixels remaining in the image with MNP after each iteration of edge exclusion; and
terminating the edge exclusion process if the number of pixels remaining in the image is equal to MNP.

7. The method of claim 4 further comprises:
defining a minimum number of pixels (MNP) remain after edge exclusion processing;

comparing the number of pixels remaining in the image with MNP after each iteration of edge exclusion;
terminating the edge exclusion process if the number of pixels remaining in the image is less than MNP; and
reinstating the pixels removed in the current iteration of edge exclusion processing.

8. The method of claim 7 wherein reinstating the pixels removed comprises:
reinstating the pixels with higher GLVs before the pixels with lower GLVs in a BVC defect site until the image has the number of pixels equal to MNP; or
reinstating the pixels with lower GLVs before the pixels with higher GLVs in a DVC defect site until the image has the number of pixels equal to MNP.

9. The method of claim 4 wherein the edge exclusion process is terminated when there is at least one pixel remaining.

10. The method of claim 1 wherein categorizing the defect comprises:
determining a defect grey level value (DGLV) for the defect site by averaging the GLVs of the remaining pixels;
determining a threshold DGLV defining an acceptable range for a killer defect; and
comparing the DGLV for the defect site with the threshold DGLV.

11. The method of claim 10 further comprises:
categorizing the defect as a killer defect if the DGLV is greater than the threshold DGLV and categorizing the defect as a non-killer defect if the DGLV is less than or equal to the threshold DGLV in a BVC defect site; or
categorizing the defect as a killer defect if the DGLV is less than the threshold DGLV and categorizing the defect as a non-killer defect if the DGLV is greater than or equal to the threshold DGLV in a DVC defect site.

12. The method of claim 1 wherein the GLV of the pixel is derived from subtracting a measured GLV by a reference GLV.

13. The method of claim 12 wherein the GLV of the pixel comprises:
a positive GLV relating to a bright voltage contrast (BVC); or
a negative GLV relating to a dark voltage contrast (DVC).

14. The method of claim 13 further comprises:
processing the image to determine outer edge pixels of the defect site,
wherein the outer edge pixels comprises pixels with a change in polarity in GLV.

15. The method of claim 14 wherein excluding outer edge pixels comprises:
defining an edge exclusion number (EEN) to indicate the number of iterations of edge exclusion processes to be performed,
wherein the EEN comprises a whole number except zero which is less than the radius from the center of the defect image.

16. The method of claim 15 wherein categorizing the defect comprises:
determining a defect grey level value (DGLV) for the defect site by averaging the GLVs of the remaining pixels;
determining a threshold DGLV defining an acceptable range for a killer defect; and
comparing the DGLV for the defect site with the threshold DGLV.

17. A method of forming a device comprising:
providing a substrate containing at least a partially formed device thereon, wherein the device comprises at least one defect site;
acquiring a pixilated image of the defect site selected, wherein each pixel comprises a grey level value (GLV);
eliminating surrounding noises of the defect site;
identifying a point of the image as the center of the defect wherein the center of the defect comprises
one pixel or adjacent pixels having the highest GLV in a bright voltage contrast (BVC) defect site, or
one pixel or adjacent pixels having the lowest GLV in a dark voltage contrast (DVC) defect site;
performing a plurality of iterations to exclude outer edge pixels surrounding the center of the defect image; and
categorizing the defect as a killer defect or a non-killer defect.

18. The method of claim 17 wherein the outer edge pixels comprises pixels with a drastic change in GLV with respect to the center of the defect.

19. The method of claim 18 wherein categorizing the defect comprises:
determining a defect grey level value (DGLV) for the defect site by averaging the GLVs of the remaining pixels;
determining a threshold DGLV defining an acceptable range for a killer defect;
comparing the DGLV for the defect site with the threshold DGLV; and
categorizing the defect as a killer or non-killer defect which further comprises
categorizing the defect as a killer defect if the DGLV is greater than the threshold DGLV and categorizing the defect as a non-killer defect if the DGLV is less than or equal to the threshold DGLV in a BVC defect site, or
categorizing the defect as a killer defect if the DGLV is less than the threshold DGLV and categorizing the defect as a non-killer defect if the DGLV is greater than or equal to the threshold DGLV in a DVC defect site.

20. A system for monitoring defects comprises:
means for providing a substrate containing at least a partially formed device thereon, wherein the device comprises at least one defect site;
means for acquiring a pixilated image of the defect site selected, wherein each pixel comprises a grey level value (GLV);
means for eliminating surrounding noises of the defect site;
means for identifying a point of the image as the center of the defect;
means for performing a plurality of iterations to exclude outer edge pixels surrounding the center of the defect image; and
means for categorizing the defect as a killer defect or a non-killer defect.

* * * * *